United States Patent [19]
Sherman et al.
[11] Patent Number: 4,471,114
[45] Date of Patent: Sep. 11, 1984

[54] SEPARATION OF MANNOSE BY SELECTIVE ADSORPTION ON ZEOLITIC MOLECULAR SIEVES

[75] Inventors: John D. Sherman, Chappaqua; Chien C. Chao, Millwood, both of N.Y.

[73] Assignee: Union Carbide Corporation, Danbury, Conn.

[21] Appl. No.: 454,646

[22] Filed: Dec. 30, 1982

[51] Int. Cl.³ .......................... C07H 1/06; C13D 3/12

[52] U.S. Cl. .................................. 536/127; 127/46.1; 127/46.3; 536/1.1; 536/124

[58] Field of Search ................ 536/1.1, 124, 127, 128; 127/46

[56] References Cited

U.S. PATENT DOCUMENTS

| | | | |
|---|---|---|---|
| 2,882,244 | 4/1959 | Milton | 252/455 |
| 2,985,589 | 5/1961 | Broughton et al. | 210/34 |
| 3,130,007 | 4/1964 | Breck | 23/113 |
| 3,677,818 | 7/1972 | Casebier et al. | 127/46 R |
| 3,776,897 | 12/1973 | Ikari et al. | 260/124 R |
| 3,928,193 | 12/1975 | Melaja et al. | 210/31 C |
| 4,014,711 | 3/1977 | Odawara et al. | 536/1.1 |
| 4,029,878 | 6/1977 | Kruse | 536/1 |
| 4,083,881 | 4/1978 | Takemura et al. | 260/635 C |
| 4,173,514 | 11/1979 | Kruse | 435/94 |
| 4,182,633 | 1/1980 | Ishikawa et al. | 127/46 A |
| 4,293,346 | 10/1981 | Landis et al. | 127/46 A |
| 4,319,929 | 3/1982 | Fickel | 127/46.2 |
| 4,349,668 | 9/1982 | Neuzil et al. | 536/124 |

FOREIGN PATENT DOCUMENTS

| | | | |
|---|---|---|---|
| 1082698 | 7/1980 | Canada | 536/1.1 |
| 1540556 | 2/1979 | United Kingdom | 536/1.1 |

OTHER PUBLICATIONS

Chemtech, Aug., 1979, pp. 501, 511.

U.S. Application Serial No. 417,577, filed Sep. 13, 1982.

Wentz, et al., "Analysis of Wood Sugars in Pulp and Paper Industry Samples by HPLC", *J. Chromat. Sci.*, 20, Aug. 1982, pp. 349–352.

Olst et al., *J. Liq. Chromatography*, 2, (1), 1979, pp. 111–115.

A. J. de Rosset et al., "Industrial Applications of Preparative Chromatography, Percolation Processes, Theory and Applications, NATO Advanced Study Institute", Espinho, Portugal, Jul. 17–29, 1978.

*Primary Examiner*—Johnnie R. Brown
*Attorney, Agent, or Firm*—Gary L. Wamer

[57] ABSTRACT

A process for the separation of mannose is disclosed which comprises the selective adsorption of same on certain types of zeolitic molecular sieves. The process is especially useful for separating mannose from glucose epimerization product or plant tissue hydrolyzate, using zeolites selected from the group consisting of BaX, BaY, SrY, NaY and CaY.

14 Claims, 7 Drawing Figures

SEPARATION OF MANNOSE BY SELECTIVE ADSORPTION ON ZEOLITIC MOLECULAR SIEVES

BACKGROUND OF THE INVENTION

1. Field of the Invention

This invention relates to a process for the liquid phase separation of mannose from glucose or from other mixtures containing mannose. More particularly and in a preferred embodiment, this invention relates to such a separation by selective adsorption onto certain types of zeolitic molecular sieves.

2. Description of the Prior Art

The sugar alcohol mannitol is a widely-used, commercially-significant material. It can be used to make resins, plasticizers, detergent builders, dry electrolytic condensers, as well as sweeteners and diluent excipient for drugs. Unfortunately, the current price of mannitol is high and therefore some of these commercial applications are not economically attractive. Mannitol can be made by hydrogenation of invert sugar, which gives a syrup containing about 26% mannitol and a yield of crystalline mannitol of about 17%. The remaining 9% mannitol in the mother liquor is difficult to recover. However, mannitol can also be made by hydrogenation of mannose, the corresponding sugar, with approximately 100% yield. Mannose is thus commercially significant, because it is the most efficient raw material for the manufacture of mannitol. In addition, L-mannose has been identified as one sugar in a series of reactions designed to produce L-sucrose, a possible non-nutritive sweetener (see CHEMTECH, August, 1979, pp. 501 and 511). Furthermore, mannose is useful as a corrosion inhibitor, as a garment softening agent or as a detergent builder. It is therefore obviously commercially desirable to have and there is a need for an inexpensive and efficient source of mannose.

There are presently two major sources of mannose: by epimerization of glucose (see, e.g., U.S. Pat. Nos. 4,029,878, 4,713,514 and 4,083,881) or from hydrolysis of hemicellulose or plant tissue (see, e.g., U.S. Pat. No. 3,677,818). The epimerization reaction yields a mixture of mannose and glucose. The hydrolysis of hemicellulose is sometimes a part of the process in making pulp from wood, or a part of the process to convert plant tissue to sugars. In both cases, the raw material is not a purified hemicellulose mannan, and the product is a mixture of many mono- and di-saccharides.

The products of epimerization of glucose can be hydrogenated directly to give a high mannitol syrup, rather than producing mannitol by separating mannitol from sorbitol. Or, as an alternative, the mannose can be separated from the glucose first, then hydrogenated to make pure mannitol.

It is also known to use a cationic exchange resin (i.e., the calcium form of Rohm and Haas' Amberlite XE200) to separate mannose from glucose (see, e.g., British Pat. No. 1,540,556). However, this method seems to be inefficient. Specifically, the feed (29.0% mannose, 67.1% glucose) is first passed through a 213 cm resin column to enrich the mannose to 87%. The 87% mannose fraction is then passed through a second identical column to give a fraction which contains at most 98% mannose. In practical operation, a process like this would be both cumbersome and expensive and a better adsorbent would appear to be desirable to make the method of separation by adsorption practical.

The problem of recovering mannose from plant tissue hydrolyzate is substantially more difficult than separating mannose from glucose. The sugar mixture contains many different sugars. Besides mannose and glucose, it contains arabinose, galactose, xylose, and cellobiose. One of the possible compositions of sodium-based sulfite liquor (a typical plant tissue hydrolyzate) is:

| | |
|---|---|
| Sodium Lignosulfonate | 61.5% |
| Xylose | 3.5% |
| Arabinose | 1.5% |
| Mannose | 14.2% |
| Glucose | 5.5% |
| Galactose | 3.8% |

The mannose in such a mixture can be recovered by forming mannose bisulfite adducts (see, e.g., U.S. Pat. No. 3,677,818). In such a process, $Na_2S_2O_5$ is added to the sulfite liquor, then the mixture is seeded with sodium mannose bisulfite to promote the crystallization of adducts. The sodium mannose bisulfite is redissolved in water and mannose is regenerated by adding a bicarbonate reagent. After the decomposition reaction is complete, ethanol is added to precipitate out sodium sulfite. After several more steps, this process recovers pure mannose at 85% yield. A process like this is not only expensive, but also yields a huge amount of chemical waste, causing serious disposal problems.

U.S. Pat. No. 3,776,897 teaches methods of separating lignosulfonate from hemicellulose and mono-saccharides. Hemicellulose is first precipitated by adding a proper water-soluble solvent into the mixture. By adding more of the same solvent, lignosulfonate is separated from mono-saccharides. No specific method to recover mannose from the mono-saccharide mixture is disclosed.

Canadian Pat. No. 1,082,698 discloses a process for separating a monosaccharide from an oligosaccharide by selective adsorption onto an X or Y zeolite containing either ammonium or Group IA or IIA metal exchangeable cations. No specific data are given for separating the monosaccharide mannose from other monosaccharides or disaccharides.

Copending, commonly-assigned U.S. patent application Ser. No. 417,577, filed Sept. 13, 1982 (D-13,577), now abandoned, discloses a process for the bulk separation of inositol by selective adsorption on zeolite molecular sieves. Table III of that patent application shows a retention volume for D-mannose and a separation factor for inositol with respect to D-mannose, for a NaX zeolite.

Wentz, et al., in "Analysis of Wood Sugars in Pulp and Paper Industry Samples by HPLC", *Journal of Chromatographic Science,* Vol. 20, August, 1982, pp. 349–352, disclose a high performance liquid chromatography (HPLC) method for analyzing wood sugars (i.e., glucose, mannose, galactose, arabinose and xylose) in a pulp hydrolyzate or a spent sulfite liquor by selective adsorption onto a polystyrene/divinyl benzene cation exchange resin.

Olst, et al, in *Journal of Liquid Chromatography,* Vol. 2, No. 1, pp. 111–115 (1979), disclose a HPLC method for the analysis of glucose-fructose-mannose mixtures resulting from the commercial alkali-catalyzed production of High Fructose Syrup from glucose. An unmodified silica is employed as the adsorbent and acetonitrile as the desorbent.

SUMMARY OF THE INVENTION

The present invention, in its broadest aspects, is a process for the liquid phase separation of mannose from mannose/glucose mixtures or other solutions containing mannose by selective adsorption on cation-exchanged type X or type Y zeolite molecular sieves. The process generally comprises contacting the solution at a pressure sufficient to maintain the system in the liquid phase with an adsorbent composition comprising at least one crystalline cation-exchanged aluminosilicate type X or type Y zeolite selected from the group consisting of BaX, BaY, SrY, NaY and CaY, to selectively adsorb mannose thereon; removing the non-adsorbed portion of the solution from contact with the adsorbent; and desorbing the adsorbate therefrom by contacting the adsorbent with a desorbing agent and recovering the desorbed mannose.

DESCRIPTION OF THE PREFERRED EMBODIMENTS

Figure 1:
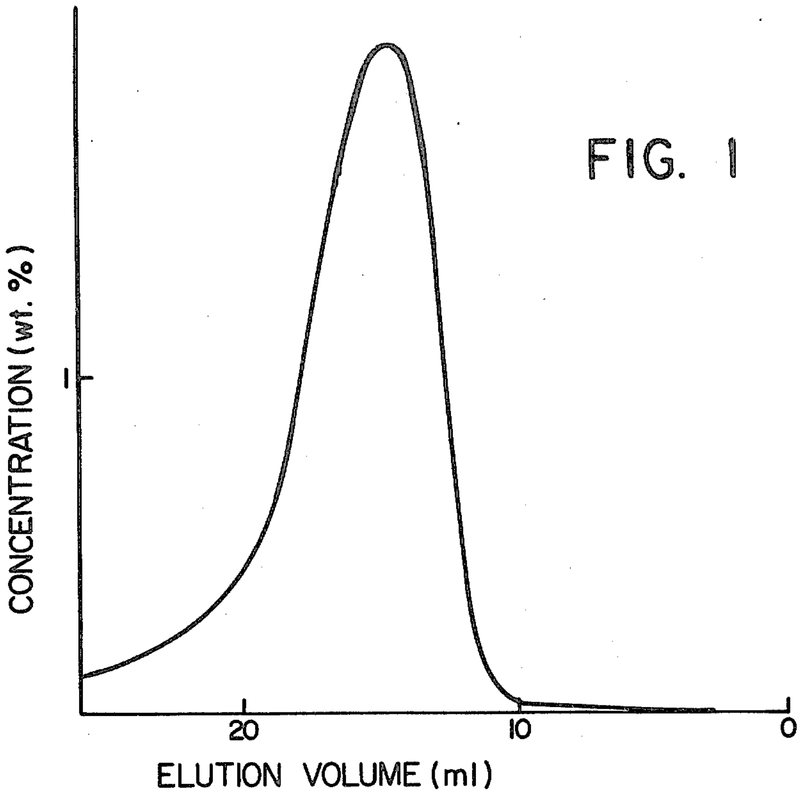
FIG. 1 shows an elution curve of a mixture of mannose and glucose where the adsorbent is a potassium-substituted zeolite type X.

The present invention provides an inexpensive, effective and simple process to recover mannose from mixtures, such as a glucose epimerization solution or a solution of plant tissue hydrolyzate. The heart of the invention is a group of zeolites with unique adsorption selectivity. The adsorption selectivities of various zeolites differ, according to their framework structure, silica-to-alumina ratio, cation type, and cation concentration. Most zeolites do not have the desired selectivity for mannose recovery. Since the sizes of the cavities inside the zeolites are of the same order of magnitude as the sizes of monosaccharides, the adsorption selectivity of a zeolite is very much dominated by steric factors and thus, is practically unpredictable.

The present inventors have discovered that certain cation forms of zeolites X and Y have excellent selectivity and kinetic properties for mannose separation. For example, it has been found that CaY has enough affinity and selectivity to be useful in mannose/glucose separations, but it may not be as useful for extracting mannose from plant hydrolyzate. On the other hand, there is a rate deficiency associated with CaX and therefore CaX may not be as useful for any mixture of monosaccharides.

The present invention provides a process for the bulk separation of mannose from feed solutions containing same. The feed solution may be, for example, a mixture of mannose and glucose derived from the epimerization of glucose; a mannose-containing plant tissue hydrolyzate such as a sodium-based sulfite liquor; or other mixtures of mannose with other carbohydrates (e.g., other wood sugars, sugar alcohols, etc.). It is expected that the process of the present invention will be useful in separating mannose from any of the foregoing feed solutions. However, for purposes of convenience only, the discussion which follows will merely generally describe the present invention in terms of separating mannose from feed solutions containing same, although it is to be expressly understood that the present invention is expected to be useful in separating mannose from any of the feed solutions identified above. For example, the process of the present invention may be employed to separate mannose from glucose and/or any of the other so-called wood sugars (i.e., arabinose, galactose, or xylose). In addition, it is expected that the process of the present invention would be equally useful for separations of the L- as well as the D- forms of the foregoing sugars.

As stated above, the product of glucose epimerization contains mannose and glucose; and hemicellulose hydrolysis products (e.g. sodium-based sulfite liquors) contain mannose and some or all of the other wood sugars. Such products may be further processed to convert some of their components or to separate and/or purify the liquid. Therefore, as used herein, "glucose epimerization product" and "hemicellulose hydrolysis product" include not only the direct liquid product of these processes but also any liquid derived therefrom such as by separation, purification or other processing.

Zeolite molecular sieves (hereinafter "zeolites") are crystalline aluminosilicates which have a three-dimensional framework structure and contain exchangeable cations. The number of cations per unit cell is determined by its silica-to-alumina molar ratio and the cations are distributed in the channels of the zeolite framework. Carbohydrate molecules can diffuse into the zeolite channels, and then interact with the cations and be adsorbed onto them. The cations are, in turn, attracted by the aluminosilicate framework which is a gigantic, multiply-charged anion.

The adsorption selectivity of the zeolite depends on the concerted action of a number of factors, as pointed out above, and hence the adsorption selectivities of zeolites are highly unpredictable. In fact, the present inventors have found that most zeolites do not adsorb mannose particularly strongly. However, BaX, BaY, SrY, NaY and CaY zeolites have been discovered to adsorb mannose substantially more strongly than other wood sugars. Therefore, they are particularly suitable for mannose recovery. Since BaY has the highest mannose selectivity, it is the preferred zeolite and would be expected to be the most useful in most applications. However, it is possible that in certain applications other zeolites may be a more practical choice considering the initial cost of the zeolite, the difficulty or expense of removing cation impurities in the final product, etc.

Zeolite Y and the method for its manufacture are described in detail in U.S. Pat. No. 3,130,007, issued Apr. 21, 1954 to D. W. Breck. Zeolite X and the method for its manufacture are described in detail in U.S. Pat. No. 2,882,244, issued Apr. 14, 1959 to R. M. Milton. The disclosures of both of said patents are hereby incorporated herein by reference.

The zeolites useful in the present invention are BaX, BaY, SrY, NaY, CaY and mixtures thereof. By "mixtures thereof" is meant both single zeolites whose sodium cations are exchanged by more than one of barium, strontium and/or calcium and physical mixtures of more than one of BaX, BaY, SrY, NaY and CaY zeolites. Typically, X and Y zeolites are prepared in sodium form and the sodium cations may be partially or wholly exchanged by different cations, such as barium, strontium and/or calcium, using known techniques. For purposes of the present invention, the above-identified useful zeolites may by only partially or may be wholly cation exchanged. For example, the cations of a BaY zeolite may be substantially all barium or only partially barium with the balance being either other useful divalent cations (i.e., strontium or calcium) or monovalent cations such as sodium or potassium. The degree of cation exchange is not critical as long as the desired degree of separation is achieved.

Data suggest that specific cation-sugar interactions are responsible for the unique sorption selectivities exhibited by the various cation forms of the X and Y zeolites useful in the invention. It is known that the number of exchangeable cations in the zeolites will decrease as the $SiO_2/Al_2O_3$ molar ratio increases and also that, as the monovalent $Na^+$ ions are replaced by divalent $Ca^{++}$, $Sr^{++}$, and/or $Ba^{++}$ ions, the total number of cations per unit cell decreases. It is also known that within the X and Y crystal structures there exist many different sites at which the cations may be located, and that some of these sites are located in positions outside of the supercages in these crystal structures. Since the sugar molecules will enter only the supercage portions of the crystal structure, it is expected that they will interact strongly only with those cations located within or on the edge of the supercages. The number and locations of the Ca, Sr and Ba cations in each crystal structure will therefore depend upon the sizes and numbers of the cations present and the $SiO_2/Al_2O_3$ molar ratio of the X or Y zeolite. While not wishing to be bound by theory, it is also expected that optimal sorption selectivity will be obtained when particular sugar molecules are presented with an opportunity, through steric considerations, to interact with a particular number of divalent cations in or on the edge of the supercage. Therefore, it is expected that optimal sorption selectivities will exist at particular exchange levels of each of these zeolite types and may also exist at particular $SiO_2/Al_2O_3$ molar ratios.

The adsorption affinities of various zeolites for different sugars was determined by a "pulse test". This test consisted of packing a column with the appropriate zeolite, placing it in a block heater to maintain constant temperature, and eluting sugar solutions through the column with water to determine the retention volume of solute. Measurements were made with powder zeolites as well as bonded aggregates of the BaY and SrY zeolites. The retention volume of solute is defined as elution volume of solute minus "void volume". "Void volume" is the volume of solvent needed to elute a non-sorbing solute through the column. A soluble polymer of fructose, inulin, which is too large to be sorbed into the zeolite pores, was chosen as the solute to determine void volume.

The elution volume of inulin was first determined. The elution volumes of the five above-identified wood sugars and cellobiose were then determined under similar experimental conditions. The retention volumes were calculated and are recorded in Table I, below. From the retention volume data, the separation factors (S.F.), $$\alpha^{Mannose}_{Glucose} \quad \alpha^{Mannose}_{Arabinose} \quad \alpha^{Mannose}_{Galactose}$$

$$\alpha^{Mannose}_{Xylose} \text{ and } \alpha^{Mannose}_{Cellobiose}$$

were calculated in accordance with the following typical equation:

$$S.F._{M/G} = \alpha^{Mannose}_{Glucose} = \frac{\text{(retention volume for mannose peak)}}{\text{(retention volume for glucose peak)}}$$

A $S.F._{M/G}$ factor greater than unity indicates that the particular adsorbent was selective for mannose over glucose and similarly for the other separation factors shown in Table II. The separation factor values calculated according to the above-mentioned method are found in Table II. All of the X-type zeolites in Tables I and II have a $SiO_2/Al_2O_3$ molar ratio of about 2.5 and all of the Y-type zeolites have a $SiO_2/Al_2O_3$ molar ratio of about 4.8–5.

TABLE I

Corrected Retention Volumes of Sugars (in mls)

Column Dimension: 40 cm length × 0.77 cm ID
Flow Rate: 0.53 gpm/ft$^2$
Temperature: 160° F.

| Zeolite Powder | Inulin | Mannose | Arabinose | Galactose | Glucose | Xylose | Cellobiose |
|---|---|---|---|---|---|---|---|
| KX | 0 | 6.3 | 7.4 | 5.8 | 6.0 | 6.6 | 2.2 |
| NaX | 0 | 1.5 | 2.0 | 1.0 | 1.5 | 1.0 | >0.5 |
| NaY | 0 | 2.7 | 2.7 | 2.6 | 1.7 | 1.7 | 1.0 |
| CaY | 0 | 2.9 | 2.9 | 1.6 | 1.2 | 0.7 | — |
| SrY* | 0 | 4.0 | 4.1 | 3.9 | 2.2 | 2.2 | 0.8 |
| BaX | 0 | 8.2 | 16.8 | 4.0 | 3.0 | 5.4 | 0.4 |
| BaY** | 0 | 37.3 | 23.6 | 27.6 | 14.4 | 8.9 | — |

**160 cm column length of 30 × 50 mesh granules.
*20 × 40 mesh granules

TABLE II

Separation Factors of Sugars

| Zeolite | αMannose Glucose | αMannose Arabinose | αMannose Galactose | αMannose Xylose | αMannose Cellobiose |
|---|---|---|---|---|---|
| KX | 1.05 | 0.85 | 1.09 | 0.95 | 2.9 |
| NaX | 1.0 | 0.75 | 1.5 | 1.5 | >3.0 |
| NaY | 1.6 | 1.0 | 1.04 | 1.6 | 2.7 |
| CaY | 2.4 | 1.0 | 1.8 | 4.1 | — |
| SrY | 1.8 | 1.0 | 1.0 | 1.8 | 5.0 |
| BaX | 2.7 | 0.5 | 2.1 | 1.5 | 20.5 |
| BaY | 2.6 | 1.6 | 1.4 | 4.2 | — |

Based on the data in Tables I and II, BaY is the most suitable zeolite for mannose separation. Relatively speaking, it adsorbs mannose more strongly than arabinose, galactose, glucose, xylose and cellobiose. It can be used to separate mannose from its epimer, glucose, but also it is particularly suitable for recovering mannose from the hydrolyzate of hemicellulose, because mannose is the last sugar to be eluted. Depending on the conditions of the elution, mannose can be collected as a pure product (e.g., at a low flow rate, with a longer column, etc.) or as a mixture with some contamination of galactose (e.g., at a higher flow rate, with a shorter column, etc.). It has also been found that BaX has better selectivity for mannose/galactose separation than BaY. It is also feasible for one to use a two-stage process to recover mannose from hydrolyzate of hemicellulose. In other words, BaY may be first used to extract mannose and some galactose from the hydrolyzate, then BaX is used to separate mannose from galactose.

BaX can also be used to extract mannose from hemicellulose hydrolyzate. Since BaX adsorbs mannose much more strongly than galactose, glucose, xylose and cellobiose, and, in turn, arabinose such more strongly than mannose it is possible to separate the mixture into three fractions, with mannose being collected in the middle fraction. Commonly-assigned, copending U.S. patent application Ser. No. 454,655, filed on even date herewith discloses a process for the bulk separation of L-arabinose from mixtures of same with other sugars for example.

As an alternative process, BaX can be used to separate arabinose and mannose from the rest of the sugars. Then, in a separate bed, arabinose may be separated from mannose. BaX, BaY, SrY, CaY and NaY can be used to separate mannose from glucose. BaX and BaY are better adsorbents than SrY, CaY and NaY. They have a higher affinity, as well as a higher selectivity, than SrY, CaY and NaY. The separation can be carried out in a moving bed scheme, or in a chromatographic elution scheme, as discussed below in more detail. If the latter is used, pure mannose can be produced by a single pass through a single bed. NaX, KX, KY, CsX, CsY, $NH_4X$, $NH_4Y$, MgX, MgY and CaX are unsuitable for this application.

In separating mannose by the process of the present invention, a bed of solid zeolite adsorbent is preferentially loaded with adsorbates, the unadsorbed or raffinate mixture is removed from the adsorbent bed, and the adsorbed mannose is then desorbed from the zeolite adsorbent by a desorbent. The adsorbent can, if desired, be contained in a single bed, a plurality of beds in which conventional swing-bed operation techniques are utilized, or a simulated moving-bed counter-current type of apparatus, depending upon the zeolite and upon which adsorbate is being adsorbed. Thus, one can employ a chromatographic elution method (such as that described in U.S. Pat. No. 3,928,193, the disclosure of which is hereby incorporated herein by reference) to recover mannose in pure form.

Various modifications of this process are possible and will be obvious to those skilled in the art. For example, after loading the zeolite bed to near the point at which mannose begins to break through and appear in the effluent, the feed can be switched to a stream of pure mannose in water, which can be passed through the bed to displace the non-mannose components from the sorbent and from the void spaced in the bed. When these non-mannose components have been adequately displaced from the bed, the bed can be desorbed with water to recover the mannose from the sorbent and voids. For example, a fixed bed loading/co-current product purge/counter-current desorption cycle may be particularly attractive when the mannose is present at low concentrations and it is desired to recover it at higher purity levels.

A preferable method for practicing the process of this invention is separation by chromatographic column. For example, a chromatographic elution method may be employed. In this method, feed solution (e.g., glucose epimerization product or hemicellulose hydrolysis product) is injected as a "slug" for a short period of time at the top of a column and eluted down through the column with water. As the mixture passes through the column, chromatographic separation leads to a zone increasingly enriched in the adsorbed sugar. The degree of separation increases as the mixture passes further down through the column until a desired degree of separation is achieved. At this point, the effluent from the column may be first shunted to one receiver which collects a pure product. Next, during the period of time when there is a mixture of sugars emerging from the column, the effluent may be directed towards a "receiver for mixed product". Next, when the zone of adsorbed sugar emerges from the end of the column, the effluent may be directed to a receiver for that product.

As soon as the chromatographic bands have passed far enough through the column, a new slug is introduced at the entrance of the column and the whole process cycle is repeated. The mixture which exits from the end of the column between the times of appearance of the pure fractions may be recycled back to the feed and passed through the column again, to extinction.

The degree of separation of the peaks as they pass through this chromatographic column will increase as the column length is increased. Therefore, one can design a column of sufficient length to provide a desired degree of separation of the components from each other.

Therefore, it is also possible to operate such a process in a mode which will involve essentially no recycle of an unseparated mixture back to the feed. However, if high purities are required, such a high degree of separation may require an exceptionally long column. In addition, as the components are eluted through the column, their average concentrations gradually decline. In the case of the sugars being eluted with water, this would mean that the product streams would be increasingly diluted with water. Therefore, it is highly likely that an optimum process (to achieve high degrees of purity of the components) should involve the use of a much shorter column (than would be required for complete separation of the peaks) and also involve separating out the portion of the effluent containing the mixture of peaks and recycling it to feed, as discussed above.

Another example of a chromatographic segaration method is a simulated moving bed process (e.g., as described in U.S. Pat. Nos. 2,985,589, 4,293,346, 4,319,929 and 4,182,633; and A. J. de Rosset et al "Industrial Applications of Preparative Chromatography", Percolation Processes, Theory and Applications, NATO Advanced Study Institute, Espinho, Portugal, July 17–29, 1978 the disclosures of which are hereby incorporated herein by reference) which could be used for extracting mannose from hemicellulose hydrolysis product. It is possible to use BaY alone to produce pure mannose in a single-stage simulated moving bed process. However, it is impossible to use BaX alone in a single-stage simulated moving bed process to produce pure mannose, because for such a process only the least strongly adsorbed or most strongly adsorbed adsorbate can be produced in pure form. It is also possible to design a two-stage process using, for example, BaY in the first stage to extract mannose and some galactose in one cut (from arabinose+xylose+glucose) and then to use BaX in the second stage to separate mannose from galactose.

In the operation of a simulated moving-bed technique, the selection of a suitable displacing or desorbing agent or fluid (solvent) must take into account the requirements that it be capable of readily displacing adsorbed adsorbate from the adsorbent bed and also that a desired adsorbate from the feed mixture be able to displace adsorbed desorbing agent from a previous step.

Figure 7:
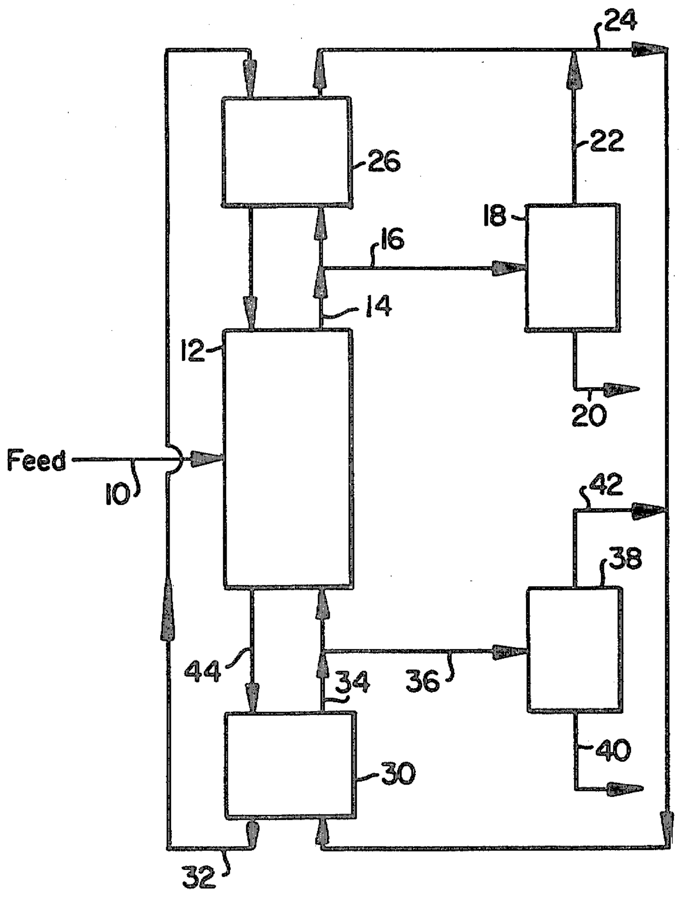
FIG. 7 shows one method in which the process of this invention may be employed.

Another method for practicing the process of this invention is illustrated by the drawing in FIG. 7. FIG. 7 represents the principles of operation of a simulated moving bed system. In the exemplified method, a number of fixed beds may be connected to one another by conduits which are also connected to a special valve (e.g., of the type described in U.S. Pat. No. 2,985,589). The valve sequentially moves the liquid feed and product takeoff points to different positions around a circular array of the individual fixed beds in such a manner as to simulate countercurrent motion of the adsorbent. This process is well-suited to binary separations.

In the drawings, FIG. 7 represents a hypothetical moving-bed countercurrent flow diagram involved in carrying out a typical process embodiment of the present invention. With reference to the drawing, it will be understood that whereas the liquid stream inlets and outlets are represented as being fixed, and the adsorbent mass is represented as moving with respect to the counter flow of feedstock and desorbing material, this representation is intended primarily to facilitate describing the functioning of the system. In practice, the sorbent mass would ordinarily be in a fixed bed with the liquid stream inlets and outlets moving periodically with respect thereto. Accordingly, a feedstock such as glucose epimerization product is fed into the system through line 10 to adsorbent bed 12 which contains particles of zeolite adsorbent in transit downwardly therethrough. The component(s) of the feedstock are adsorbed preferentially on the zeolite particles moving through bed 12, and the raffinate is entrained in the liquid stream of water desorbing agent leaving bed 12 through line 14 and a major portion thereof is withdrawn through line 16 and fed into evaporation apparatus 18 wherein the mixture is fractionated and the concentrated raffinate is discharged through line 20. The water desorbing agent leaves the evaporation apparatus 18 through line 22 and is fed to line 24 through which it is admixed with additional desorbing agent leaving the adsorbent bed 26, and is recycled to the bottom of adsorbent bed 30. The zeolite carrying adsorbed sugar passes downwardly through line 44 into bed 30 where it is counter-currently contacted with recycled desorbing agent which effectively desorbs the sugar therefrom before the adsorbent passes through bed 30 and enters line 32 through which it is recycled to the top of adsorbent bed 26. The desorbing agent and desorbed sugar leave bed 30 through line 34. A portion of this liquid mixture is diverted through line 36, where it passes evaporation apparatus 38, and the remaining portion passes upwardly through adsorbent bed 12 for further treatment as hereinbefore described. In evaporation apparatus 38, the desorbing agent and sugar are fractionated and the sugar product is recovered through line 40 and the desorbing agent is either disposed of or passed through line 42 into line 24 for recycle as described above. The undiverted portion of the desorbing agent/raffinate mixture passes from bed 12 through line 14, enters bed 26 and moves counter-currently upwardly therethrough with respect to the desorbing agent-laden zeolite adsorbent passing downwardly therethrough from recycle line 32. The desorbing agent passes from bed 26 in a relatively pure form through recycle line 24 and to bed 30 as hereinbefore described.

In the foregoing processes, the desorbing agent employed should be readily separable from admixture with the components of the feed-stock. Therefore, it is contemplated that a desorbing agent having characteristics which allow it to be easily fractionated or volatilized from those components should be used. For example, useful desorbing agents include water, mixtures of water with alcohols, ketones, etc. and possibly alcohols, ketones, etc, alone. The preferred desorbing agent is water.

While it is possible to utilize the activated adsorbent zeolite crystals in a non-agglomerated form, it is generally more feasible, particularly when the process involves the use of a fixed adsorption bed, to agglomerate the crystals into larger particles to decrease the pressure drop in the system. The particular agglomerating agent and the agglomeration procedure employed are not critical factors, but it is important that the bonding agent be as inert toward the adsorbate and desorbing agent as possible. The proportions of zeolite and binder are advantageously in the range of 4 to 20 parts zeolite per part binder on an anhydrous weight basis. Alternatively, the agglomerate may be formed by pre-forming zeolite precursors and then converting the pre-form into the zeolite by known techniques.

The temperature at which the adsorption step of the process should be carried out is not critical and will depend on a number of factors. For example, it may be desirable to operate at a temperature at which bacterial growth is minimized. Generally, as higher temperatures are employed, the zeolite may become less stable although the rate of adsorption would be expected to be higher. However, the sugar may degrade at higher temperatures and selectivity may also decrease. Furthermore, too high a temperature may require a high pressure to maintain a liquid phase. Similarly, as the temperature decreases, the sugar solubility may decrease, mass transfer rates may also decrease and the solution viscosity may become too high. Therefore, it is preferred to operate at a temperature between about 4° and 150° C., more preferably from about 20° to 110° C. Pressure conditions must be maintained so as to keep the system in liquid phase. High process temperatures needlessly necessitate high pressure apparatus and increase the cost of the process.

It may be desirable to provide a small amount of a soluble salt of the zeolite cation in the feed to the adsorbent bed in order to counteract any stripping or removal of cations from the zeolite in the bed. For example, with barium-exchanged zeolite, a small amount of a soluble barium salt, such as barium chloride, etc., may be added to the feed or desorbent in order to provide a sufficient concentration in the system to counteract stripping of the barium cations from the zeolite and maintain the zeolite in the desired cation-exchange form. This may be accomplished either by allowing the soluble barium concentration in the system to build up through recycle or by adding additional soluble barium salt when necessary to the system.

The pH of the fluids in the process of the present invention is not critical and will depend upon several factors. For example, since both zeolites and sugars are more stable near a neutral pH and since extremes of pH's might tend to degrade either or both of the zeolites and sugars, such extremes should be avoided. Generally, the pH of the fluids in the present invention should be on the order of about 4 to 10, preferably about 5 to 9.

The following Examples are provided to illustrate the process of the present invention as well as a process which does not separate mannose. However, it is not intended to limit the invention to the embodiments in the Examples. All examples are based on actual experimental work.

As used in the Exmples appearing below, the following abbreviations and symbols have the indicated meaning:

| | |
|---|---|
| KX | Potassium-exchange zeolite X |
| CaY | Calcium-exchanged zeolite Y |
| BaX | Barium-exchanged zeolite X |
| BaY | Barium-exchanged zeolite Y |
| $gpm/ft^2$ | gallons per minute per square foot |

EXAMPLE 1

A 40 cm column having an inside diameter of 0.77 cm was loaded with KX zeolite powder. The column was filled with water and maintained at a temperature of 160° F. Water was then pumped through the column and a flow rate of 0.53 $gpm/ft^2$ was maintained. For a period of one minute, the feed was switched to a mixture which contained 2% mannose by weight and 2% glucose by weight, and then switched back to water. The composition of the effluent from the column was monitored by a refractometer. FIG. 1 of the drawings shows the concentration profile of the effluent. Mannose and glucose emerged from the KX column as a single peak and were not significantly separated.

EXAMPLE 2

Figure 2:
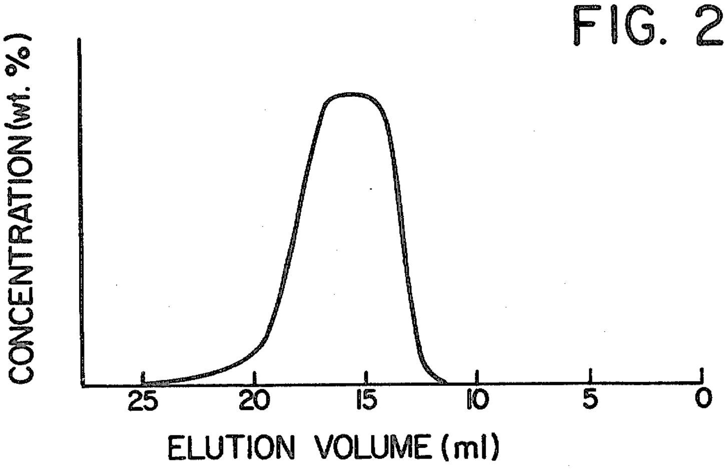
FIGS. 2–4 show elution curves of the same mannose/glucose mixture where the adsorbents are a calcium-substituted type Y zeolite, a barium-substituted type X zeolite and a barium-substituted type Y zeolite, respectively.

The same column and experimental conditions as in Example 1 were used except that the zeolite used was CaY powder. FIG. 2 gives the concentration profile of the effluent. The glucose peak emerges before the mannose peak. The two are partially resolved.

EXAMPLE 3

Figure 3:
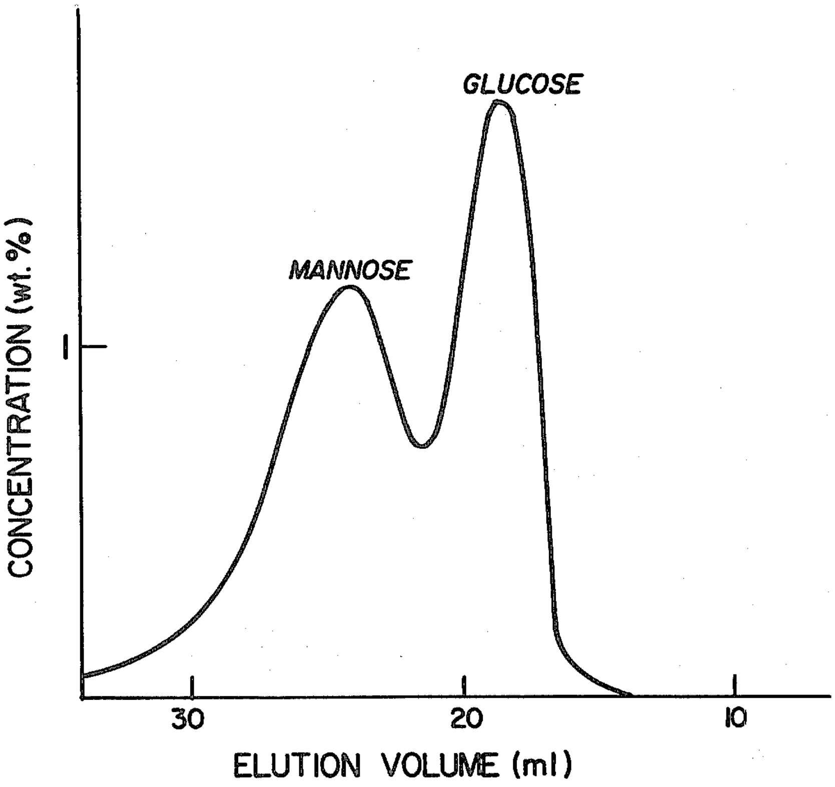

The same column and experimental conditions as in Example 1 were used except that the zeolite in the column was BaX powder. FIG. 3 gives the concentration profile of the effluent. The peak of glucose emerges before the peak of mannose. They are substantially resolved.

EXAMPLE 4

Figure 4:
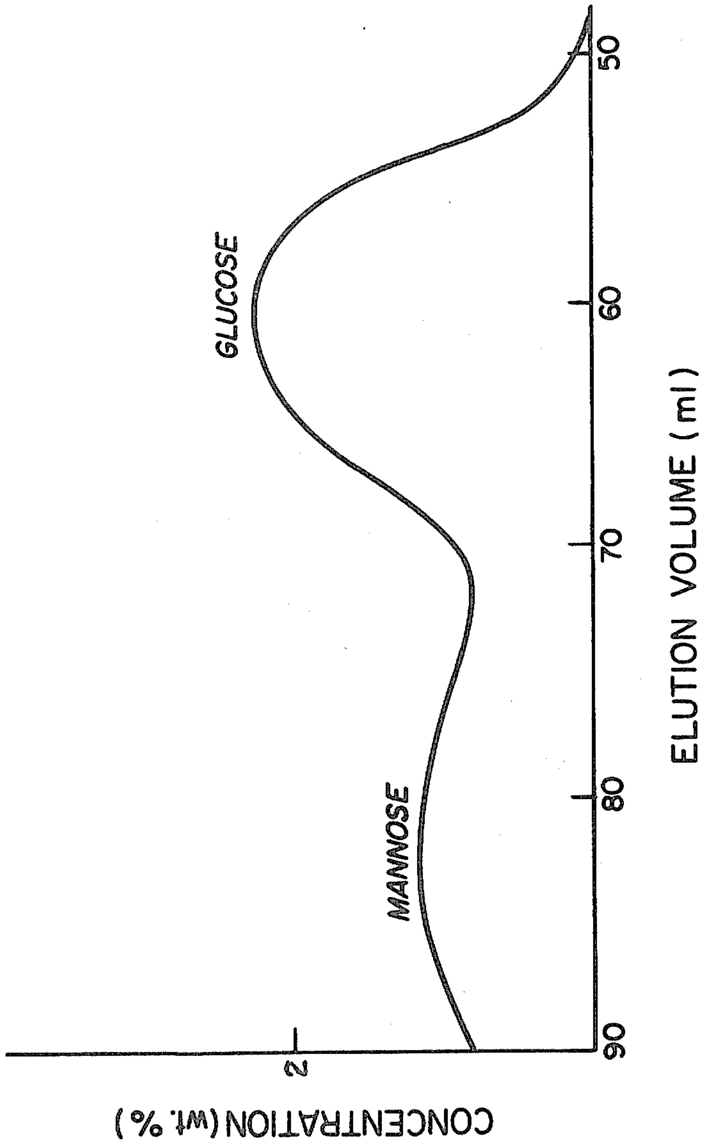

A 160 cm column having an inside diameter of 0.77 cm was loaded with 30×50 mesh of BaY aggregates, which contained 20% clay binder. The column was filled with water and maintained at 160° F. Water was pumped through the column and a flow rate of 0.53 $gpm/ft^2$ was maintained. For a period of two minutes the feed was switched from water to an aqueous solution which contained 7% mannose and 13% glucose, by weight, then switched back to water. The effluent from the column was monitored by a refractometer. FIG. 4 gives the concentration profile of the effluent. This is a single-pass, single-column experiment. In the effluent, about 70% of the mannose is glucose-free, and about 70% of the glucose is mannose-free.

EXAMPLE 5

Figure 5:
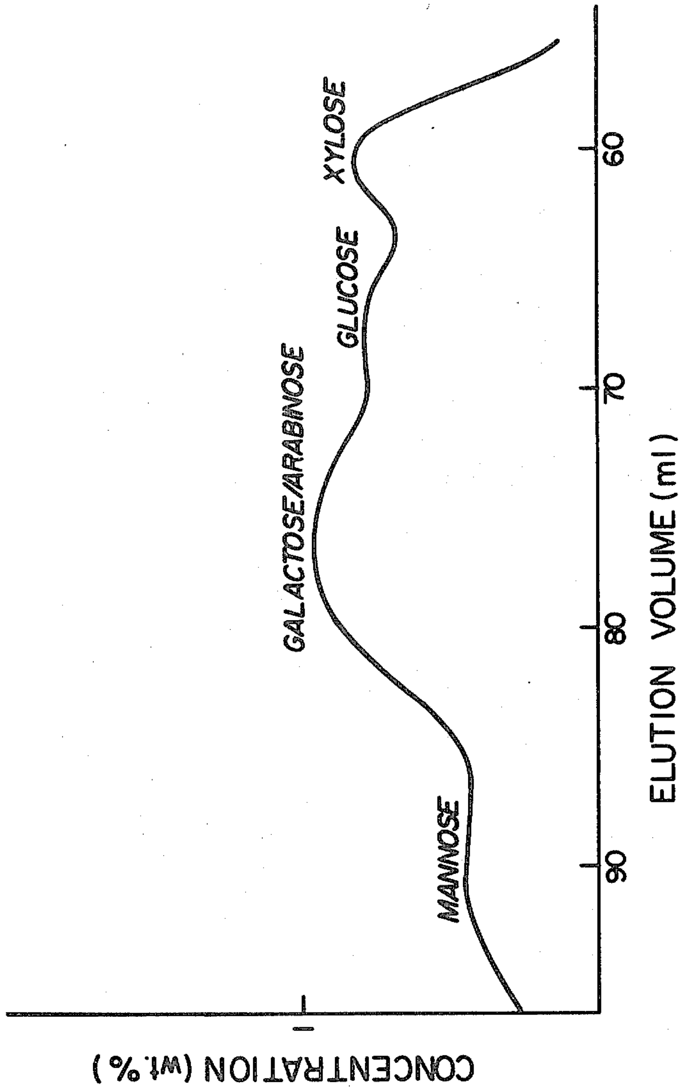
FIG. 5 shows an elution curve of a mixture containing mannose, arabinose, galactose, glucose and xylose, where the adsorbent is a barium-substituted type Y zeolite.

The same column and experimental conditions as in Example 4 were used except that the flow rate and the composition of the sugar mixture are different. The sugar mixture now contains 2% mannose, 2% arabinose, 2% galactose, 2% glucose and 2% xylose, by weight. FIG. 5 gives the concentration profile of the effluent, when the flow rate was maintained at 0.1 $gpm/ft^2$. A substantial portion of the mannose peak is free from contamination by the other sugars.

EXAMPLE 6

Figure 6:
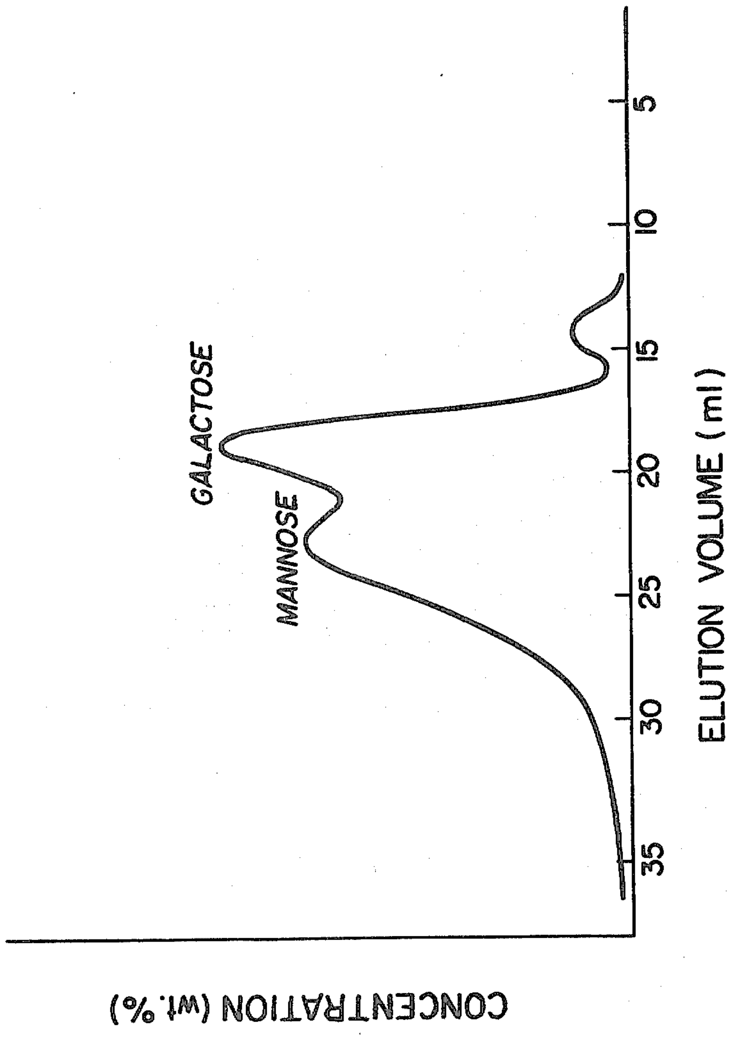
FIG. 6 shows an elution curve of a mixture of mannose and galactose where the adsorbent is a barium-substituted type X zeolite.

The same column and experimental conditions as in Example 3 were used, except that the flow rate was 0.26 $gpm/ft^2$ and the sugar mixture contained 2% mannose and 2% galactose, by weight. FIG. 6 gives the concentration profile of the effluent. Reasonably good separation between mannose and galactose was achieved with this 40 cm column.

It is, of course, well-known to those skilled in the art that in chromatographic-type separations of these types, improvements in the degrees of observed separation are to be expected when longer columns are employed, when smaller quantities of sorbates are injected, when smaller zeolite particles are used, etc. However, the above results are sufficient to demonstrate to those skilled in the art the technical feasibility of performing these separations by the use of any type of chromatographic separation processes known in the art. Furthermore, various fixed bed loading/regeneration type of cyclic adsorption processes can also be employed to perform the above separations.

The following Table III summarizes the compositions of the various zeolites employed in the foregoing examples:

TABLE III

| | Cation Exchange Level in Zeolite (Equivalent Percent)* | | | | |
|---|---|---|---|---|---|
| Zeolite | Na+ | K+ | Ca++ | Sr++ | Ba++ |
| KX | 21 | 79 | — | — | — |
| CaY | 14 | — | 86 | — | — |
| BaX | 1 | — | — | — | 99 |
| BaY | 30 | — | — | — | 70 |

*($[R_{2/n}{}^{n+}O]/[Na_2O + K_2O + BaO]$) mole ratio × 100.

What is claimed is:

1. A selective adsorption process for the separation of mannose from a mixture containing mannose and at least one of glucose, arabinose, xylose and galactose which comprises contacting said mixture of mannose and at least one of glucose, arabinose, xylose and galactose at a pressure sufficient to maintain the system in the liquid phase with an adsorbent composition comprising at least one crystalline aluminosilicate zeolite selected from the group consisting of BaX, BaY, SrY, NaY, CaY and mixtures thereof, whereby mannose is selectively adsorbed thereon, removing the non-adsorbed portion of said mixture from contact with the zeolite adsorbent and desorbing the adsorbent therefrom by contacting said adsorbent with a desorbing agent and recovering the desorbed adsorbate.

2. A process in accordance with claim 1 wherein the temperature is from about 4° C. to about 150° C.

3. A process in accordance with claim 1 wherein the temperature is from about 20° C. to about 110° C.

4. A process in accordance with claim 1 wherein the desorbent is selected from the group consisting of water and mixtures thereof with alcohols or ketones.

5. A process in accordance with claim 1 wherein the desorbent is water.

6. A process in accordance with claim 1 wherein said mixture contains mannose and glucose.

7. A process in accordance with claim 1 wherein said mixture contains mannose and at least one of glucose, arabinose, xylose and galactose, and wherein said zeolite is BaY.

8. A process in accordance with claim 1 wherein said mixture comprises the hydrolysis product of plant tissue.

9. A process in accordance with claim 1 wherein said mixture comprises sodium-based sulfite liquor.

10. A process in accordance with claim 1 wherein said mixture comprises the epimerization product of glucose.

11. A process for separating mannose from the epimerization product of glucose which contains mannose and glucose, by selective adsorption which comprises contacting said product at a temperature of from about 4° C. to 150° C. and at a pressure sufficient to maintain the system in the liquid phase with an adsorbent composition comprising at least one crystalline aluminosilicate zeolite selected from the group consisting of BaX, BaY, SrY, NaY, CaY and mixtures thereof, whereby the mannose is selectively adsorbed thereon, removing the non-adsorbed portion of said product from contact with the zeolite adsorbent, and desorbing the mannose therefrom by contacting said adsorbent with a desorbing agent and recovering the desorbed mannose.

12. A process for separating mannose from plant tissue hydrolyzate by selective adsorption which comprises contacting said hydrolyzate at a temperature of from about 4° C. to 150° C. and a pressure sufficient to maintain the system in the liquid phase with an adsorbent composition comprising at least one crystalline aluminosilicate zeolite selected from the group consisting of BaX, BaY, SrY, NaY, CaY and mixtures thereof whereby the mannose is selectively adsorbed thereon, removing the non-adsorbed portion of said hydrolyzate from contact with the zeolite adsorbent, and desorbing the mannose therefrom by contacting said adsorbent with a desorbing agent and recovering the desorbed mannose.

13. A two-stage process for separating mannose from plant tissue hydrolyzate which contains mannose, glucose, arabinose, xylose and galactose, by selective adsorption which comprises contacting in a first stage said hydrolyzate at a temperature of from about 4° C. to 150° C. and at a pressure sufficient to maintain the system in the liquid phase with an adsorbent composition comprising a BaY crystalline aluminosilicate zeolite whereby a mixture of mannose and galactose are selectively adsorbed, removing the non-adsorbed portion of said hydrolyzate from contact with the zeolite adsorbent, desorbing the mixture of mannose and galactose therefrom by contacting said adsorbent with a desorbing agent; contacting in a second stage said mixture at a temperature of from about 4° C. to 150° C. and at a pressure sufficient to maintain the system in the liquid phase with an adsorbent composition comprising a BaX crystalline aluminosilicate zeolite whereby mannose is selectively adsorbed thereon, removing the non-adsorbed portion of said mixture from contact with the zeolite adsorbent and desorbing the mannose therefrom by contacting said adsorbent with a desorbing agent and recovering the desorbed mannose.

14. A process for separating mannose from plant tissue hydrolyzate by selective adsorption which comprises contacting said hydrolyzate at a temperature of from about 4° C. to 150° C. and a pressure sufficient to maintain the system in the liquid phase with an adsorbent composition comprising a BaY zeolite whereby the mannose is selectively adsorbed thereon, removing the non-adsorbed portion of said hydrolyzate from contact with the zeolite adsorbent, and desorbing the mannose therefrom by contacting said adsorbent with a desorbing agent and recovering the desorbed mannose.

* * * * *

UNITED STATES PATENT AND TRADEMARK OFFICE
CERTIFICATE OF CORRECTION

PATENT NO. : 4,471,114
DATED : September 11, 1984
INVENTOR(S) : J.D. Sherman, C.C. Chao It is certified that error appears in the above—identified patent and that said Letters Patent is hereby corrected as shown below:

Col. 6, Table 1, Heading Cellobiose,"> 0.5" should read -- < 0.5 --.

Signed and Sealed this

*Fourteenth* Day of *May 1985*

[SEAL]

*Attest:*

DONALD J. QUIGG

*Attesting Officer* *Acting Commissioner of Patents and Trademarks*